United States Patent [19]

Scheglov et al.

[11] Patent Number: 5,041,090
[45] Date of Patent: Aug. 20, 1991

[54] OCCLUDING DEVICE

[76] Inventors: Viktor I. Scheglov, Belorusskaya, 15b, kv. 51; Alexandr I. Goncharov, generala Koltsova, 40, kv. 39; Vyacheslav G. Antonenko, Volgo-Donskaya, 67, kv. 4; Alexandr G. Savenko, deceased, late of Kiev; by Lidia I. Osaulenko, administrator, ulitsa Murashko, 5, kv. 100; Igor A. Savenko, administrator, prospekt Geroev Stalingrada, 27A, kv. 479, all of Kiev; Grigory M. Savenko, administrator, ulitsa Ostrovskogo, 56 Belaya tserkov, Kievskaya oblast; Julia A. Savenko, heir, ulitsa Murashko, 5, kv. 100, Kiev, all of U.S.S.R.

[21] Appl. No.: 415,262
[22] PCT Filed: Jan. 12, 1988
[86] PCT No.: PCT/SU88/00010
  § 371 Date: Aug. 2, 1989
  § 102(e) Date: Aug. 2, 1989
[87] PCT Pub. No.: WO89/06551
  PCT Pub. Date: Jul. 27, 1989

[51] Int. Cl.⁵ ............................................. A61M 29/00
[52] U.S. Cl. .................................... 604/101; 606/195
[58] Field of Search .................... 604/96–103; 606/194, 195, 191; 128/899

[56] References Cited

U.S. PATENT DOCUMENTS

| | | | |
|---|---|---|---|
| 3,173,418 | 3/1965 | Baran | 604/101 |
| 3,834,394 | 9/1974 | Hunter et al. | 606/195 |
| 4,282,875 | 8/1981 | Serbinenko et al. | 606/195 |
| 4,311,146 | 1/1982 | Wonder | 606/195 |
| 4,364,392 | 12/1982 | Strother et al. | 606/195 |
| 4,403,612 | 9/1983 | Fogarty | 606/194 |
| 4,423,725 | 1/1984 | Baran et al. | 604/101 |
| 4,471,779 | 9/1984 | Antoshkiw et al. | 606/195 |
| 4,545,367 | 10/1985 | Tucci | 606/195 |
| 4,638,803 | 1/1987 | Rand | 606/195 |
| 4,773,393 | 9/1988 | Haber et al. | 606/195 |
| 4,802,479 | 2/1989 | Haber et al. | 606/195 |
| 4,819,637 | 4/1989 | Dormandy, Jr. et al. | 606/195 |

Primary Examiner—C. Fred Rosenbaum
Assistant Examiner—William W. Lewis
Attorney, Agent, or Firm—Burgess, Ryan & Wayne

[57] ABSTRACT

An occluding device, comprising an inflatable balloon (1) interconnected through a sphincter (2) with an insertable catheter (3), and an additional balloon (4) accommodated inside the main balloon (1) and having its own catheter (5), whereas one of the balloons has through perforations in the surface thereof.

2 Claims, 2 Drawing Sheets

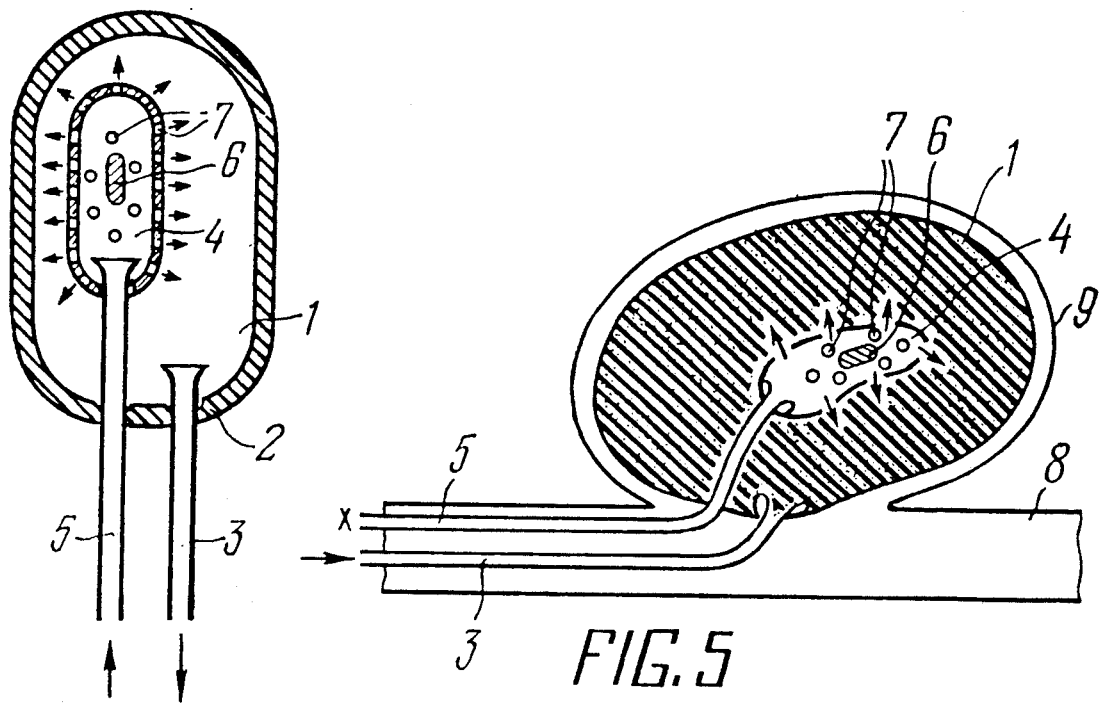
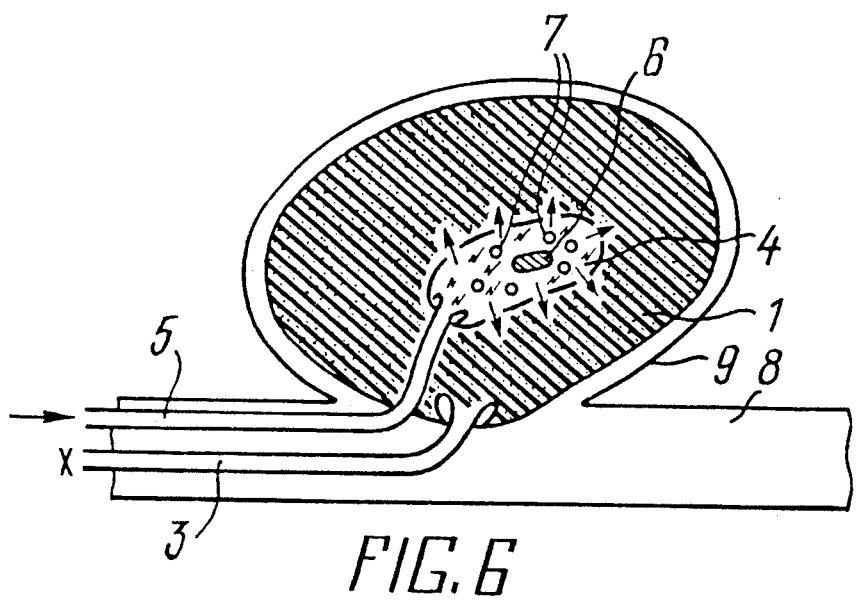

OCCLUDING DEVICE

TECHNICAL FIELD

The invention relates generally to medicine, more specifically to radiological surgery (or surgical radiology) and has particular reference to occluding devices which are applicable for treatment of various vascular diseases, preferably large-sized diversely shaped aneurysms.

BACKGROUND OF THE INVENTION

One of the most widespread diseases affecting humans nowadays are vasculopathies of the brain, heart, and other organs. It is surgical treatment that is the most efficacious way of remedying the vascular diseases. Apart from adequately effective surgical techniques such treatment methods incorporate some negative aspects, e.g., high degree of traumatism, especially in cases of cerebrovascular surgery, and severe postoperative complications. Radiological surgery that has gained progress recently is featured by a lower degree of traumatism, a lesser amount of postoperative complications and makes it possible to carry out operative management of vasculopathies in such areas that are amenable neither to conventional vascular surgery nor to microsurgery of blood vessels. Especially hardly amenable to treatment by virtue of radiological surgery are extensive and giant aneurysms, false aneurysms as well as wide-neck aneurysms. At present treatment of the aforesaid aneurysms by the radiological surgery techniques boils down to stationary occlusion of blood vessels carrying the aneurysm. As a rule, such surgical procedures involve gross postoperative complications resulting from ischemia of large tissue areas, especially those of the brain.

Imperfection of the current radiological-surgery instruments impedes successful solution of one of the major problems one now faces in the field of treatment of vasculopathies.

Further progress of radiological surgery has called for the provision of basically novel occluding devices for performing the surgical procedures mentioned above.

One state-of-the-art occluding device (cf. GB 2,045,621, A) is known to comprise a detachable inflatable balloon intercommunicating with the catheter through an adapter coupling. The balloon is detached from the catheter by burning out the coupling, using an electric heating coil connected to a current source through wire conductors, which are passed inside the catheter, while the heating coil is insulated from the surrounding atmosphere through an additional dielectric sleeve. Such a construction arrangement of the balloon-catheter unit provides for more reliable detachment of the balloon from the catheter but renders it rigid, which prevents the construction from penetrating into the aneurysmal sac or chamber and the efferent vessels. Operative procedures with the use of balloon-catheters of the given type are aimed at stationary occlusion of the afferent vessels and the aneurysm-carrying vessels. This results in a drastic change of the circulation in a given region and in the development of some ischemia-affected areas.

The aforementioned events are extremely undesirable, especially in cases of radiological surgery on cerebral vessels.

The device mentioned above makes it possible in some cases to penetrate into the chambers of extensive and giant aneurysms and wide-neck aneurysms. However, one balloon is insufficient for such aneurysms to cut out of the blood flow, whereas introduction of many such balloons does not provide their interconnection, and their migration within the aneurysmal sac due to the blood flow results in their being expelled from the aneurysms and in occlusion of the vitally important vessels.

One more prior-art balloon-catheter is known to comprise separate balloons and communicating ducts or passages (cf. DE 3,048,923 $C_2$). The device incorporates two balloons, one of them being a positioning balloon, i.e., that aimed at holding the device in a required place, while the other balloon is the occluding one. Upon having been inflated both of the balloons acquire the same shape of various configuration. Separate passages are for separate injection of a contrast medium and the components of a quick-setting polymer. The device under consideration makes it possible to set the polymerization time of a quick-setting polymer due to the provision of independent passages (catheters) for filling the interior of a balloon, thus enabling one to separately feed the components of quick-setting polymer to the balloon in a required ratio thereof. The balloon-catheter, having such a construction arrangement is adapted for closure of the interventricular and atrial septal defects and has therefore but a restricted application due to its narrow-specified purpose.

There is in common use currently the Debrun's balloon-catheter (cf. FR, A, 2,383,673). The device is essentially a detachable inflatable balloon provided with a radiopaque marker which is made as a metallic clip located in a thickened ballon portion arranged opposite to the sphincter thereof. The sphincter of the balloon is curved inwards into the interior of the balloon and of the catheter placed on the balloon outer wall. Upon cutting the vessel (aneurysm) out of circulation the balloon is distended by being filled with a quick-setting polymer, while the catheter is removed and the balloon sphincter is turned inside out. To remove (detach) the balloon from the catheter, use is made of a movable larger-diameter catheter placed on the working (main) catheter. The catheters are moved in the opposite directions, viz, the main catheter is withdrawn, while the accessory catheter is moved towards the balloon, thus helping to remove the balloon from the working catheter, whereupon both of the catheters are taken out of the vessel. The Debrun's balloon-catheter features a rigid construction, thereby not providing penetration of the balloon into the efferent vessels and sacs of an aneurysm, which restricts practical application of the device. Moreover, surgical procedures carried out with the aid of the Debrun's balloon-catheter are as a rule aimed at stationary occlusion of the afferent vessels carrying aneurysms, which affects badly the blood supply and involves post-operative morbid events. Even in cases of successful attempts to put the Debrun's balloon-catheter into the chamber of extensive and giant aneurysms and wide-neck aneurysms, as many as ten ballons are necessary to be brought into the aneurysmal sac for the aneurysm to be cut out of circulation. However, such a great number of the balloons fail to be retained in the aneurysmal sac and get expelled therefrom by virtue of the blood flow. Thus, vascular aneurysms cut out of blood flow develop recurrent bleeding in many a case.

SUMMARY OF THE INVENTION

The object of the present invention is to provide such an occluding device that, due to being equipped with an additional balloon, would make it possible to cut most diversely shaped extensive aneurysms out of blood flow with high degree of reliability.

This object is accomplished by an occluding device, comprising a detachable inflatable ballon interconnected through a sphincter to an insertable catheter, according to the invention, is provided with an additional balloon having a radiopaque marker and its own catheter, the additional ballon being accommodated inside the main balloon, one of the balloons having through perforations in its surface.

This enables one to solve the problem of the so-called "dead" catheter space, and to separately feed to the aneurysmal sac the thrombosing adhesive and the components of a quick-setting polymer, thereby making it possible to determine and control the polymerization time of the quick-setting polymer in the balloon interior.

It is due to the device of the invention that extensive differently shaped aneurysms that have previously been unamenable to treatment now are curable by virtue of radiological surgery.

SUMMARY OF THE DRAWINGS

In what follows the invention being claimed will be illustrated by a description of some specific embodiments thereof to be considered with reference to the accompanying drawings, wherein:

FIG. 4 is a general diagrammatic view of a device showing perforations in the wall of the inner balloon, according to the invention;

FIG. 5 represents the device of FIG. 4 while in action, according to the invention; and FIG. 6 depicts schematically an exemplary separate delivery of the components of a quick-setting polymer to the aneurysmal sac, according to the invention.

PREFERRED EMBODIMENT OF THE INVENTION

Figure 1:
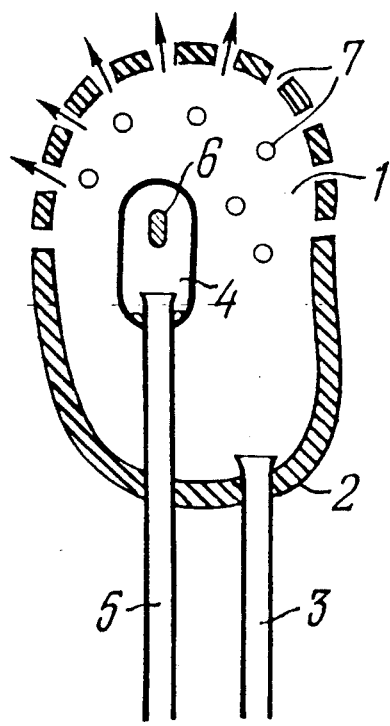
FIG. 1 is a general diagrammatic view of an occluding device showing perforations in the outer balloon, according to the invention.

The occluding device as claimed in this invention comprises an outer inflatable balloon 1 (FIGS. 1, 4) interconnected through a sphincter 2 to an insertable catheter 3. According to the invention, the device is provided with an additional balloon 4 having its own catheter 5, a radiopaque marker 6 being accommodated inside the additional balloon 4, while the balloon 1 has through perforations 7.

A radiological surgery is preceded by determining the therapy tactics and the kind of a balloon to be used, namely, provision of perforations in the inner or outer balloon.

Figure 2:
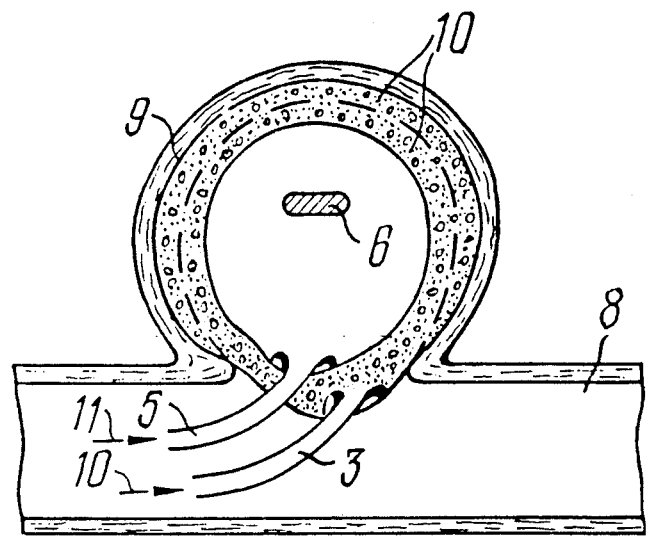
FIG. 2 illustrates the device of FIG. 1 while in action, according to the invention.
Figure 3:
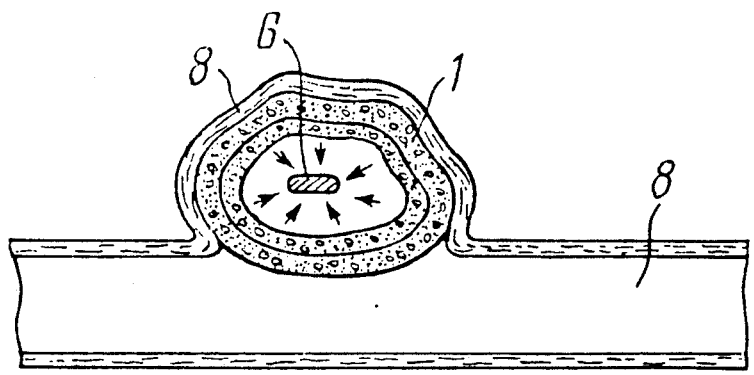
FIG. 3 shows an exemplary cutting of an extensive aneurysm out of the blood flow upon injection of the balloon and disconnecting the catheter therefrom, according to the invention.

The balloon 1 accommodating the balloon 4 which incorporates the radiopaque marker 6, is injected, by way of the catheters 3, 5 and through a puncture needle into an arterial vessel 8 to be delivered to the sac of an aneurysm 9 (FIGS. 2, 5). The radiopaque marker 6 enables one to monitor the position of the balloons 1, 4 in the sac of the aneurysm 9. Then, depending on the kind of surgery, fed to the balloon 1 along the catheter 3 is a required filler, i.e., an adhesive 10 and a principal component 11 of the quick-setting polymer. To complete the surgery, there are fed to the balloon 4 along the catheter 1 (FIG. 6) the lacking components of the filler for the balloons. FIG. 3 presents the terminating stage of the surgery.

When an extensive arterial aneurysm with a wide (normal) neck is diagnosed, there is selected an occluding device featuring through perforations in the outer balloon (FIG. 1) for a roentgenosurgical procedure to perform. Once the patient has been given medicinal premedication, his/her artery is punctured. Then the balloons 1, 4 and the catheters 3, 5 introduced through the puncture needle are approached, under the roentgenotelevision guidance, to the opening of the aneurysm 9, along the artery 8, and the balloons 1, 4 are inserted into the chamber of the aneurysm 9. Next a radiopaque matter is injected into the balloon 4 along the catheter 5, at the same time effecting roentgenotelevision monitoring until complete obturation of the chamber of the aneurysm 9 occurs.

Thereupon the radiopaque matter is let out through the catheter of the balloon 4 and its volume is measured, after which a quick-setting polymer, e.g., silicone is injected into the balloon 4 along the catheter 5 till obturation of the neck of the aneurysm 9. Then a thrombosing adhesive 10 is injected with a syringe along the catheter 3 into the interior of the balloon 1, said adhesive making its way via the through perforations 7 into the chamber of the aneurysm 9, thereby reliably bonding the walls of the balloons 1, 4 and the wall of the aneurysm 9 (FIG. 2) together. Once the quick-setting polymer has polymerized, the catheters 3, 5 are detached from the balloons 1, 4 using any heretofore-known techniques. Upon further polymerization the silicone 12 reduces in volume and entrains the bonded-together walls of the balloons 1, 4 and of the aneurysm 9, with the result that the volume of the former aneurysm 9 (FIG. 3) is diminished.

Having diagnosed a medium-size intricate-configuration wide-neck aneurysm, one should select for a roentgenosurgical procedure an occluding device provided with through perforations in the inner balloon (FIG. 4). Then the balloons 1, 4 (FIG. 2) along with the catheters 3, 5 are advanced to the aneurysmal opening and introduced into the aneurysmal sac under the roentgenotelevision guidance and by virtue of the arterial blood hemodynamics. Next the balloon 1 is filled with the principal component of a quick-setting polymer through the catheter 3 until complete obturation of the sac of the aneurysm 9, which is well checked angioscopically. Thereupon a present amount of catalyst is syringe-injected along the catheter 5 into the interior of the balloon 4, after which the catalyst penetrates via the through perforations 7 of the balloon 4 to the interior of the balloon 1, thus causing rapid polymerization of the principal component of the quick-setting polymer 12 (FIG. 6). Once the quick-setting polymer has polymerized, the catheters 3, 5 are detached from the balloons 1, 4 using one of the heretofore-known techniques, whereupon control serial angiography is performed.

INDUSTRIAL APPLICABILITY

The occluding device of the present invention is largely adapted for cutting out of the blood flow medium-size, extensive and giant aneurysms of major large-calibre vessels of the brain, neck, internal organs, etc. Cutting such aneurysms of human body out of the blood flow so far offers much difficulty when applying conventional balloon-catheters. The occluding device as claimed in the invention makes it possible to separately deliver adhesives and thrombosing matters to the aneurysmal sac and to the interior of the balloons, as well as quick-setting polymer compositions. This enables one to carry out treatment, using radiological surgery techniques, such aneurysms that have not heretofore been amenable to treatment, with high degree of reliability without relapses and with the physiological blood flow remaining unaffected. It is due to the construction features of the occluding devices claimed in the invention that a possibility is provided for a slow-rate diminishing of the volume of former aneurysms, which is especially important and valuable in treatment of cerebrovascular aneurysms, since compression produced by extensive aneurysms on the surrounding cerebral structures in reduced.

Moreover, the present occluding devices provide for reliable prevention of a possible recurrent aneurysmal laceration and hemorrhage.

We claim:

1. An occluding device comprising:
   a main inflatable balloon;
   a catheter inserted into said main inflatable balloon;
   a sphincter interconnecting said main inflatable balloon and said catheter;
   an additional inflatable balloon having perforations therein and being within said main inflatable balloon;
   a catheter inserted into said additional inflatable balloon;
   a sphincter interconnecting said additional inflatable balloon and said catheter inserted into said additional inflatable balloon.

2. The occluding device of claim 1 further comprising marker means within said additional inflatable balloon.

* * * * *

UNITED STATES PATENT AND TRADEMARK OFFICE
CERTIFICATE OF CORRECTION

PATENT NO. : 5,041,090

DATED : August 20, 1991

INVENTOR(S) : Lea, et al.

It is certified that error appears in the above-identified patent and that said Letters Patent is hereby corrected as shown below:

Column 3, last formula: Between the "$R^5$" and second "$R^3$" should be --$X\ominus$--;
Column 4, line 25: "CA 56" should read --CA $\underline{56}$--;
Column 5, line 47: "preferably" should read --preferable--;
Column 6, lines 40 & 41: "complex" should read --Complex--;
Column 7, line 44: "groups" should read --group--;
Column 8, line 46: "or" should read --of--;
Column 8, line 68: "CA56" should read --CA $\underline{56}$--;
Column 8, line 69: "42" should read --$\underline{42}$--;
Column 9, line 18: "OH" should read --$\overline{KOH}$--;
Column 9, line 23: "C)" should be added before "synthesis".

Signed and Sealed this

Twenty-third Day of November, 1993

Attest:

BRUCE LEHMAN

*Attesting Officer*     *Commissioner of Patents and Trademarks*